United States Patent [19]

Jenkins

[11] 4,191,541
[45] Mar. 4, 1980

[54] METHOD AND APPARATUS FOR GAS SAMPLE ANALYSIS

[75] Inventor: Charles W. Jenkins, Fernandina Beach, Fla.

[73] Assignee: Container Corporation of America, Chicago, Ill.

[21] Appl. No.: 933,567

[22] Filed: Aug. 14, 1978

[51] Int. Cl.$^2$ .............................................. B01D 53/14
[52] U.S. Cl. .......................................... 55/18; 55/73;
    55/93; 55/185; 55/222; 55/270; 73/421.5 R;
    422/88; 423/242
[58] Field of Search ................... 55/18, 68, 73, 87, 93,
    55/95, 185, 222, 224, 256, 270; 73/23 R, 421.5
    R, 421.5 A; 423/220, 242; 422/83, 88, 89

[56] References Cited

U.S. PATENT DOCUMENTS

| | | | |
|---|---|---|---|
| 1,374,689 | 4/1921 | Torrey | 55/256 X |
| 1,687,229 | 10/1928 | Riedel | 423/220 X |
| 2,895,335 | 7/1959 | Kraftson et al. | 73/421.5 A |
| 3,391,577 | 7/1968 | Friauf et al. | 73/421.5 R |
| 3,459,947 | 8/1969 | Cropper | 55/270 X |
| 3,581,469 | 6/1971 | Davis et al. | 55/270 X |
| 3,581,473 | 6/1971 | Ririe, Jr. et al. | 55/270 X |
| 3,733,777 | 5/1973 | Huntington | 55/185 X |
| 3,819,330 | 6/1974 | Creighton | 422/83 |
| 3,890,100 | 6/1975 | Busch | 422/89 X |
| 4,013,431 | 3/1977 | Berkel et al. | 55/93 X |
| 4,100,806 | 7/1978 | Carbonnelle et al. | 73/421.5 A |
| 4,105,508 | 8/1978 | Arod et al. | 422/88 X |

FOREIGN PATENT DOCUMENTS 2049673   3/1971   France ........................................ 55/270

Primary Examiner—Robert H. Spitzer

[57] ABSTRACT

Apparatus for withdrawing a gas from a source and conditioning the gas for subsequent analysis for total reduced sulfur content comprising a gas probe having an inlet for a stream of gas and an outlet therefor, a conduit having means to provide heat to a gas stream flowing therein extending from the probe outlet to a condenser for cooling the gas and condensing out water, a second conduit from the condenser to a vacuum which causes a gas stream to enter the probe and flow through the heatable conduit to the condenser and then the second conduit, a third conduit for delivering a stream of gas from the second conduit to a scrubber to wash the gas stream with a scrubbing liquid, a demistor for removing the gas stream from the scrubber and separating entrained scrubbing liquid, and a pump for pumping the scrubbed gas stream, from which scrubbing liquid has been removed, to an analyzer and flow meter.

A method of conditioning the gas for analysis using the apparatus is also disclosed.

21 Claims, 6 Drawing Figures

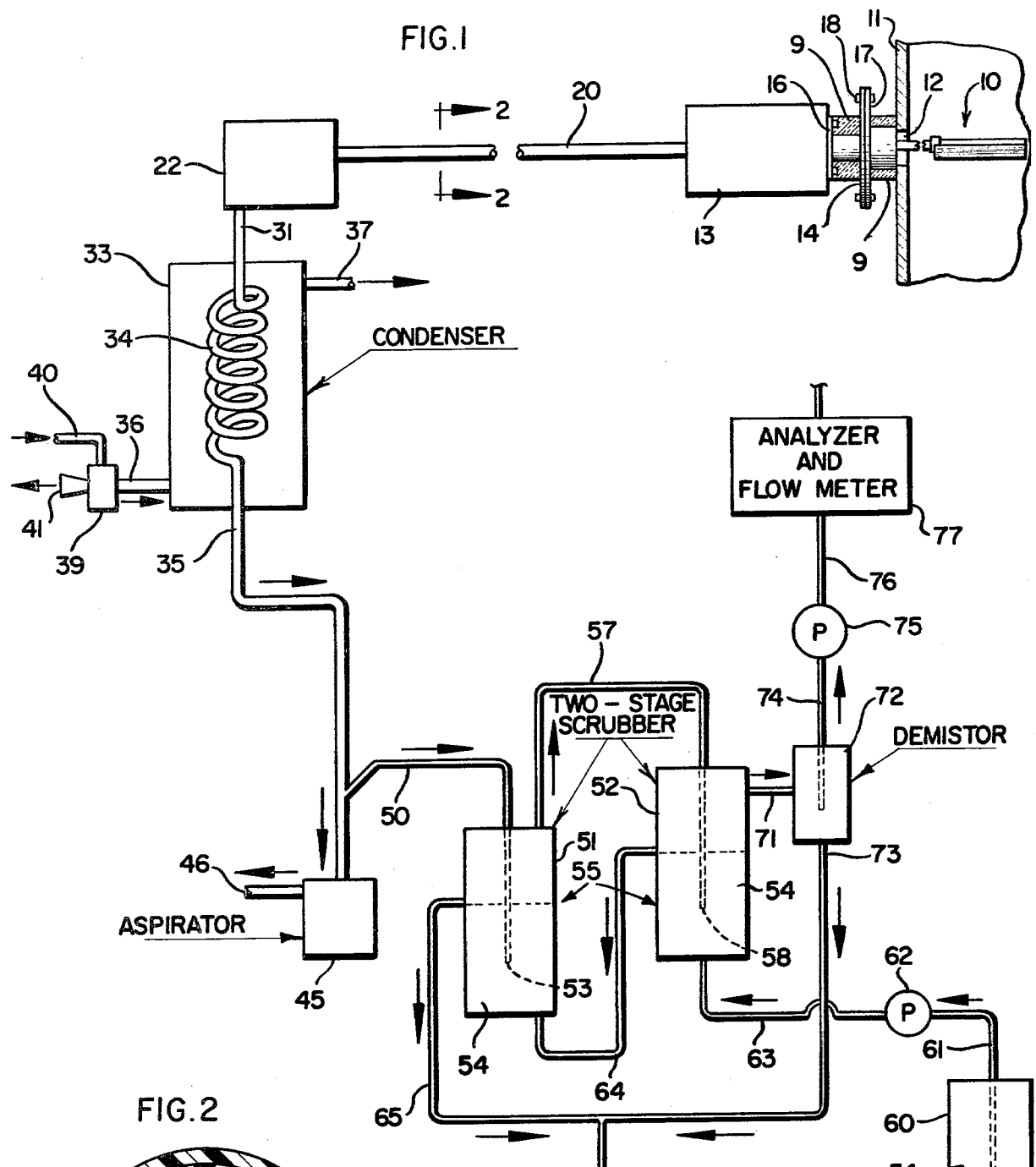
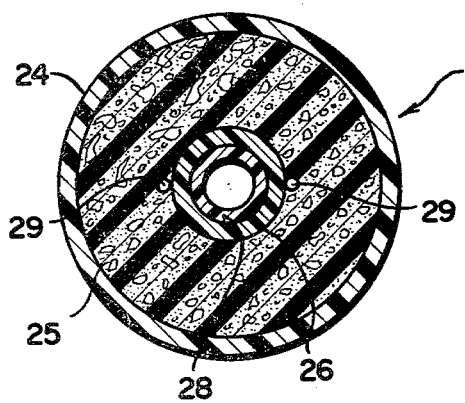

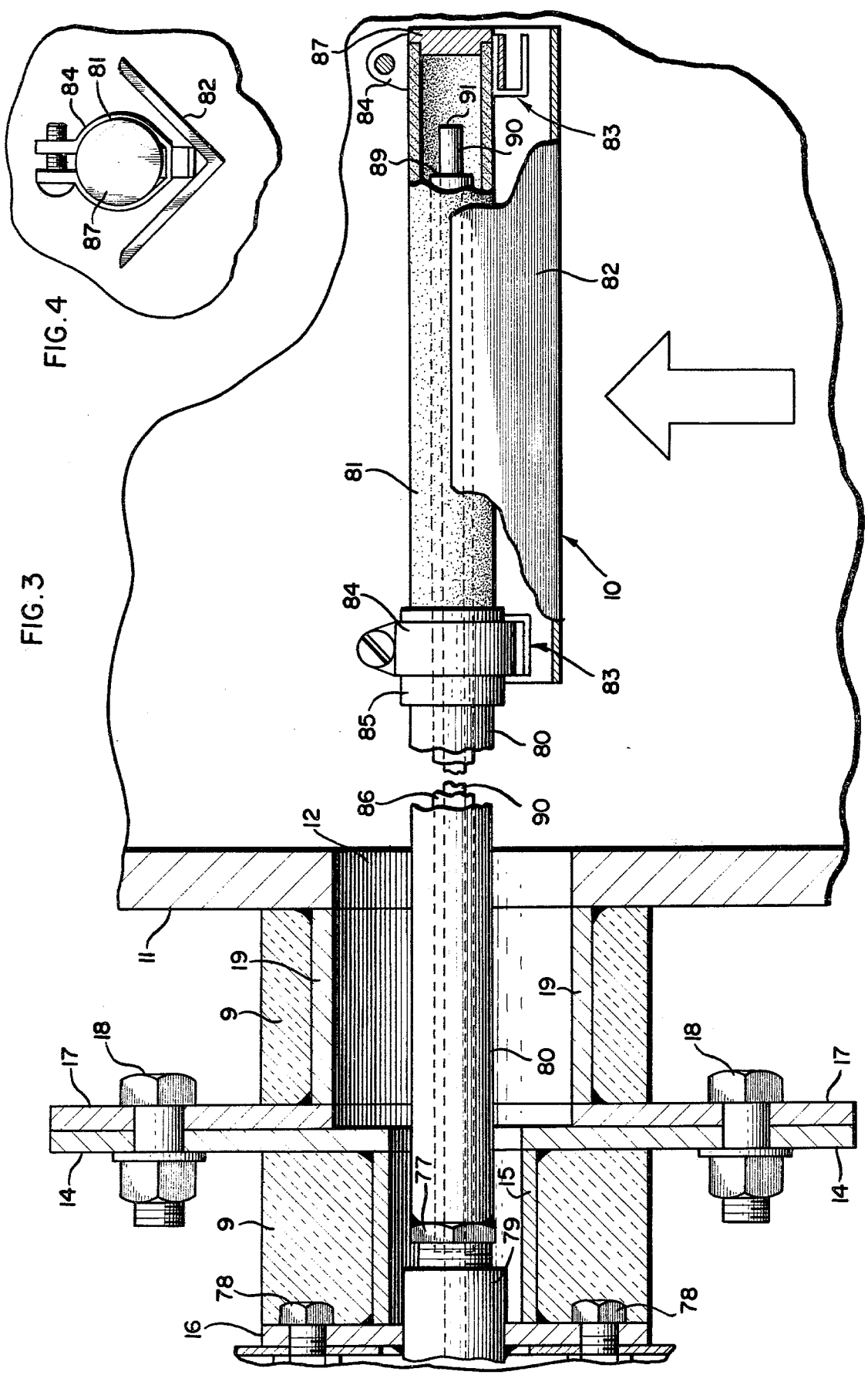

METHOD AND APPARATUS FOR GAS SAMPLE ANALYSIS

BACKGROUND OF THE INVENTION

This invention relates to apparatus and methods for monitoring the composition of a gaseous environment. More particularly, this invention is concerned with apparatus and methods for continuously sampling gases and continuously monitoring the gases for total reduced sulfur content.

Many industrial processes use fuels and chemicals which produce gases containing reduced sulfur compounds in gaseous form. Many of these reduced sulfur gases, such as hydrogen sulfide, methyl mercaptan, dimethyl sulfide and dimethyl disulfide are not only malodorous but are welfare-related pollutants. Environmental restrictions, accordingly, limit the total reduced sulfur content which gases vented to the atmosphere may contain. Industrial plants are necessarily careful to minimize the amount of reduced sulfur gases which are produced, such as by use of low sulfur-containing fuels, substitution of raw materials and by installation of gas treating equipment suitable for withdrawal of gaseous reduced sulfur compounds. In spite of all these efforts it is essential that the gas vented to the atmosphere be monitored continuously to determine that the gas standards for purity are met.

To properly monitor a waste gas for total reduced sulfur content, a sample of the gas must first be taken, usually from a flue or stack, treated as appropriate to prepare the sample for analysis by the test procedure to be employed, and then analyzed. The gas sample is usually hot with a high water content, such as 30–40% by volume, and is generally taken quite far from the location where it is analyzed. Before the gas sample is analyzed it cools, water in the sample condenses and water soluble reduced sulfur gases in the sample are adsorbed in the water thereby leaving a gas sample for analysis having less reduced sulfur gases than the initial or raw sample.

A further problem in conditioning or preparing a sample of gas to be tested is in treating it to remove sulfur dioxide which, if not removed, will lead to an inaccurate analysis for total reduced sulfur. Present methods pass the entire gas sample through a comparatively large volume of scrubbing liquid which removes the sulfur dioxide on a batch basis. This procedure requires use of a large volume of scrubbing liquid to handle gas sampling over a substantial period of time. The time needed for the gas and scrubbing liquid to reach equilibrium when a large volume of each is used, to obtain an accurate analysis, requires that the total time needed for the test extend for hours.

SUMMARY OF THE INVENTION

According to one aspect of the invention there is provided an apparatus for withdrawing a gas from a source and conditioning the gas for subsequent analysis for total reduced sulfur content. The apparatus comprises a gas probe having an inlet for a stream of gas and an outlet therefor, a conduit having means to provide heat to a gas stream flowing therein extending from the probe outlet to a condenser having a passage through which a gas stream can flow and be cooled and vapor in the gas condensed to liquid by indirect heat exchange with a cooling fluid, a second conduit from the condenser passage to a means for producing a vacuum which causes a gas stream to enter the probe and flow through the heatable conduit to and through the condenser passage and the second conduit, a third conduit for delivering a stream of gas from the second conduit to a scrubber to wash the gas stream with a scrubbing liquid, means for removing the gas stream from the scrubber and separating entrained scrubbing liquid, and means for pumping the scrubbed gas stream, from which scrubbing liquid has been removed, to an analyzer and flow meter.

A removable tube of substantially inert material, such as polytetrafluoroethylene (Teflon), is desirably placed inside of the conduit wherever convenient from about the probe to about the condenser for the gas stream to flow therethrough to maintain the gas stream out of other contact with the conduit. The tube is readily and inexpensively replaced with it shows signs of deterioration or it acquires a deposit of solid material on the interior wall.

The apparatus generally includes a means to provide a cool fluid for use in the condenser to cool the gas stream by indirect heat exchange. A vortex cooler powered by compressed air is particularly useful in developing a stream of cold air for cooling in the condenser.

Although the gas stream may be withdrawn through the probe by use of any suitable equipment which produces a vacuum, it is recommended that an aspirator be used for this purpose. Regardless of the type of equipment used to develop the vacuum, it should include a means downstream thereof for venting a major portion of the gas stream to waste so that the third conduit conveys a remaining minor portion of the gas stream to the scrubber. The second conduit is advantageously positioned to direct flow therethrough of condensed liquid from the condenser to a means downstream thereof for draining off the condensed liquid while avoiding flow of condensed liquid into the third conduit. Generally, it is desirable to have the third conduit communicate with the second conduit between the condenser and the means for producing a vacuum to facilitate diverting only a minor part of the initial gas stream into the third conduit. The third conduit is intentionally made substantially smaller diametrically than the second conduit since only a minor amount of the initial gas stream is fed to the scrubber.

Included as part of the apparatus, desirably, is means to continuously drain scrubbing liquid from the first stage at about the same rate it is received therein from the second stage. To achieve this, a scrubbing liquid reservoir container is provided together with means to withdraw scrubbing liquid from the container and feed it continuously at a uniform rate through the scrubber as the gas stream flows through the scrubber.

The described apparatus is considered to provide optimum gas sample conditioning and preparation when a continuous counter-current scrubber is used. Desirably, the counter-current scrubber has at least two stages in series, with conduit means communicating with the two stages so that scrubbing liquid can be delivered from a scrubbing liquid container by a conduit to a downstream second stage and from that stage to an upstream first stage, and from the first stage to waste.

According to a second aspect of the invention, there is provided a method comprising withdrawing a stream of hot gas containing water vapor from a source believed to contain a gaseous reduced sulfur content, continuously maintaining the withdrawn stream of hot gas at a temperature above the dew point temperature of the gas, feeding the stream of hot gas to a condensor to condense the water vapor from the gas, removing the water with a stream of cooled gas from the condenser, diverting a minor portion of the cooled gas stream substantially devoid of water to a scrubber, scrubbing the cooled gas stream in the scrubber with a scrubbing liquid, withdrawing the scrubbed gas stream from the scrubber, separating residual scrubbing liquid from the scrubbed gas stream, and feeding the scrubbed gas stream to an analyzer and flow meter to determine the total reduced sulfur content in the gas stream.

The hot gas is desirably cooled in the condenser by cold air from a vortex cooler. Also, the water and a major portion of the cooled gas stream from the condenser are continuously fed to waste.

The scrubbing liquid is desirably supplied to, and removed from, the scrubber at a uniform rate, and advantageously using continuous counter-current flow of scrubbing liquid.

The scrubbing liquid used is generally one which reacts with any sulfur dioxide in the gas stream to remove it therefrom.

BRIEF DESCRIPTION OF THE DRAWINGS

FIG. 1 illustrates diagrammatically the apparatus provided by the invention and its use in conditioning a gas sample;

FIG. 2 is a sectional view taken along the line 2—2 of FIG. 1;

FIG. 3 is an enlarged view of the probe and parts used to support it in a stack;

FIG. 4 is an end view of the probe shown in FIG. 3;

DETAILED DESCRIPTION OF THE DRAWINGS

Figure 5:
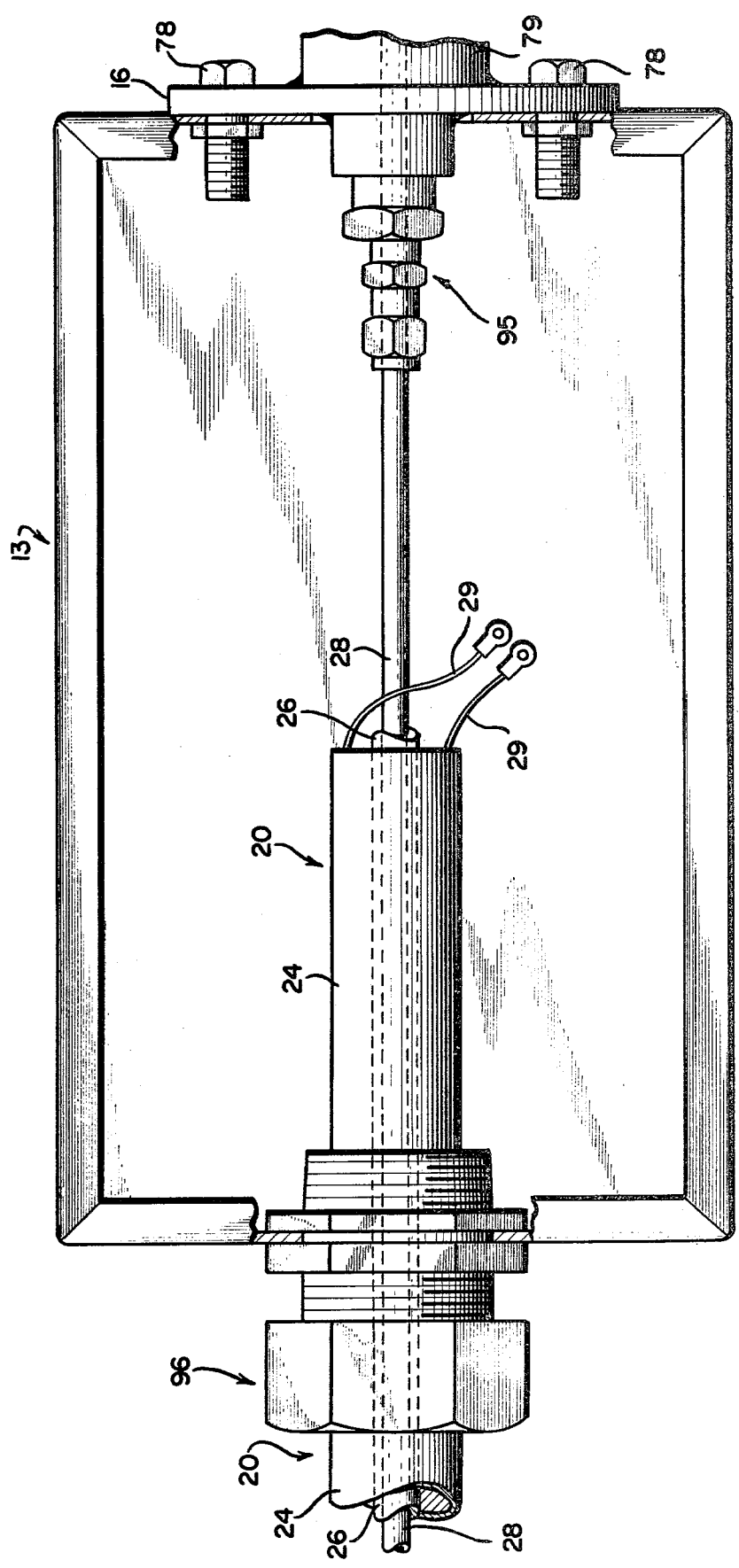
FIG. 5 is an elevational view of a first junction box which constitutes a terminus for one end of the heatable conduit.

With reference to FIG. 1, a probe 10 is located in a stack or vent, one wall 11 of which is shown. The probe passes through an opening 12 in the stack so that a representative sample of the gas to be analyzed can be withdrawn during a continuous period. The probe 10 is connected to junction box 13 by flange 16. Flange 16 and flange 14 are joined to each end of tubular member 15. The flange 14 is removably connected to a flange 17 by bolts 18. Flange 17 is joined by tubular member 19 to the stack wall 11. Insulation 9 can be placed around members 15 and 19, if desired.

Junction box 13 is desirably positioned near the stack or vent through which flows the gas to be analyzed. Conduit 20 extends from junction box 13 to a junction box 22, which desirably is at a location remote from junction box 13 but preferably is not far from the analytical equipment to be used for determining the reduced sulfur gas content of the gas which flows through the stack. Conduit 20 is heatable to maintain the gas sample at an elevated temperature above its dew point so that the water content of the gas will not condense therein. Stack gases from many industrial plants contain 30 to 40% water by volume. If this water condensed and the gases were in contact with the water for a long enough time some of the reduced sulfur compounds would dissolve in the water and thus be removed so that subsequent analysis of the sample would not accurately indicate the sulfur content.

Figure 6:
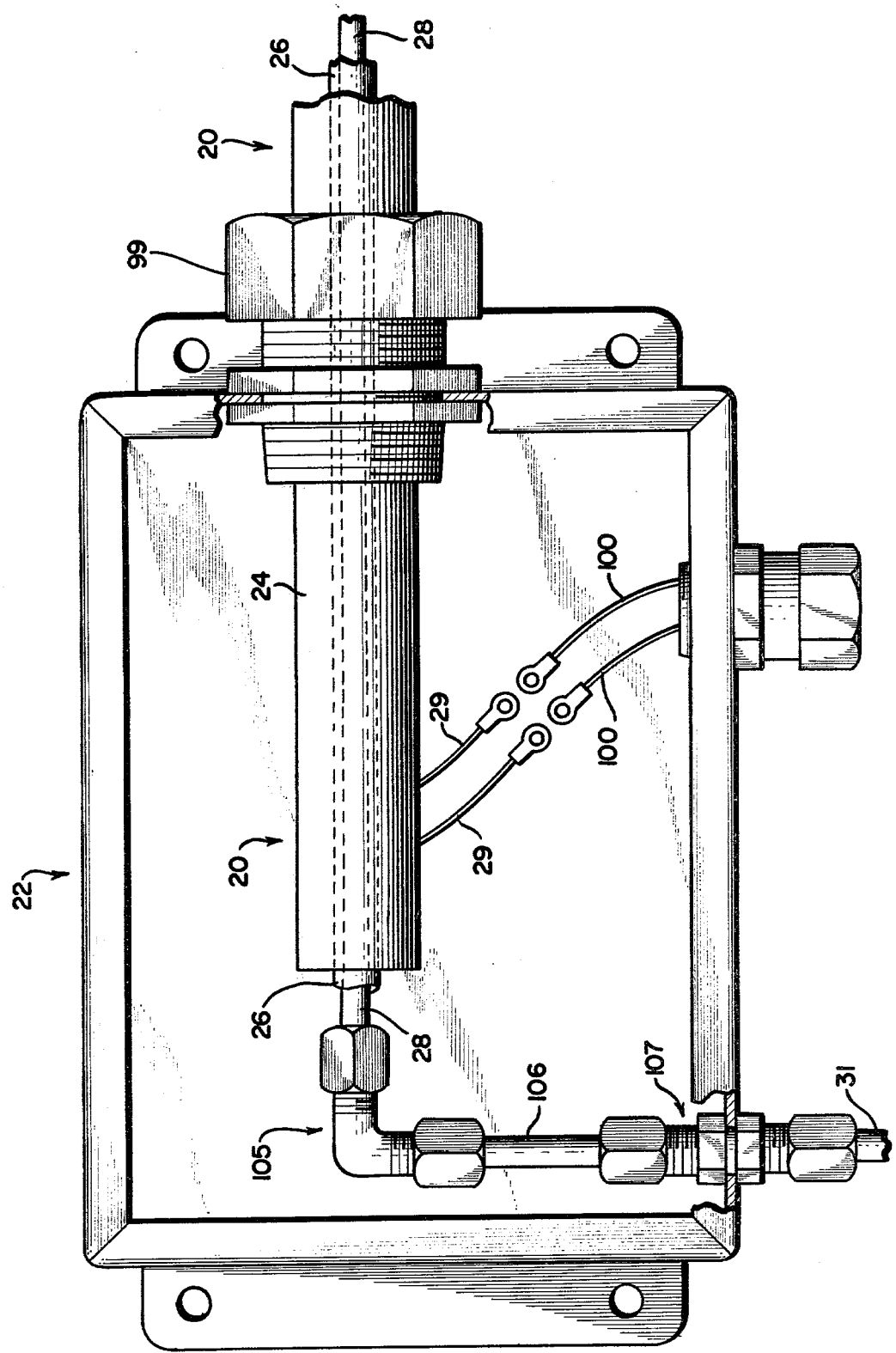
FIG. 6 is an elevational view of a second junction box which constitutes a terminus for the second end of the heatable conduit.

FIG. 2 illustrates the structure of one form of heatable conduit 20. As shown in this figure, a polyethylene sheath 24 covers a foamed insulation core 25, which has a ⅜ inch outside diameter Teflon tube 26 centrally and permanently located therein. Inside of the ⅜ inch outside diameter tube 26 is located a removable ¼ inch outside diameter Teflon tube 28. Two wires 29 located 180° apart are positioned along the outer surface of the tube 26. The two wires 29, desirably Nicrome wires, are twisted one revolution per each two linear feet of conduit. One type of commercially available heatable conduit 20 having the described structure, but without the removable ¼ inch outside diameter tube, is marketed under the name Dekoron. The removable ¼" tube 28 is employed to protect the remainder of conduit 20 from degradation by action of the hot gases. The ¼" tube can be removed periodically and be replaced by a new tube. The remainder of the conduit 20, which is at least twenty-five times more expensive than tube 28, can be continued to be used. The conduit 20 begins in junction box 13 and ends in junction box 22, as is shown more clearly in FIGS. 5 and 6. The conduit 20 will vary in length according to the installation but not uncommonly will be from 100 to 250 feet long. During travel of the gas sample from the probe through conduit 20 to junction box 22 it is kept at a temperature above the dew point, and usually no less than 240° F.

Extending from junction box 22 (FIG. 1) is conduit 31 of ¼ inch outside diameter Teflon tubing, which extends into condenser 33 and provides a passageway in the form of cooling coil 34 through which the gas sample flows and is cooled. The gas sample is desirably cooled to at least 10° F. below the surrounding or ambient temperature to assure that there will be no water condensation elewhere in the apparatus. The cooled gas sample and condensed water are removed from the condenser by means of conduit 35 which is in communication with the passageway formed by coil 34. Condenser 33, made of polyvinylchloride, is provided with a source of cold air by means of inlet conduit 36. The cooling air is removed from condenser 33 by means of conduit 37. The cold air needed to cool the condenser 33 is supplied by a vortex cooler 39 which is operated by pressurized air fed thereto by means of air supply line 40. Hot air is taken out of vortex cooler 39 through vent 41 while the cold air from the vortex cooler is directed through conduit 36 into the condenser 33. One type of vortex cooler is commercially available as the Wilkerson cooler.

The conduit 35 extends to aspirator 45 (FIG. 1) which provides a vacuum for drawing the gas sample from the vent or stack into probe 10. An aspirator of the ejector type operated by 15 to 20 psig air pressure will produce a vacuum generally suitable for withdrawing a gas sample at the rate of about 1 to 2 liters per minute. At such withdrawal rates, the gas sample has a retention time in heatable conduit 20 in the range of about 0.1 to 2 seconds, which leaves very little time for any water condensation to occur even if the temperature is low. Many gas sample temperatures initially are about 350° F. and higher. It is desired that the temperature of the gas be kept above 250° F. in conduit 20, but at least high enough above the dew point to assure that no condensation will take place.

Most of the gas sample removed from the stack through probe 10 by means of the aspirator 45 is vented through the aspirator to conduit 46 (FIG. 1) for disposal to waste. The water which condenses in condenser 33 is also removed through conduit 35 and aspirator 45, and it too is disposed of through conduit 46. Conduit 50 branches from conduit 35 between condenser 33 and aspirator 45 to withdraw or separate a minor part of the gas sample which is removed through the probe 10. Conduit 20 can be made considerably smaller than conduit 35, since generally not more than 25% of the withdrawn sample flows to conduit 50. Specifically, conduit 50 can have a ⅛ inch outside diameter and a 1/16 inch inner diameter compared to conduit 35 which has a ¼ inch outside diameter and a 3/16 inch inner diameter. The gas sample which flows through conduit 50 travels at a rate of about 250 ml per minute. Conduit 50 is joined to conduit 35 in such a way that water flowing through conduit 35 will be unable to flow into conduit 50.

As shown in FIG. 1, the conduit 50 delivers the gas sample to the first stage 51 of two-stage continuous counter-current scrubber 55. The end 53 of conduit 50 extends into a scrubbing liquid 54 in the first stage 51. After bubbling through the scrubbing liquid the gas sample is removed from the first stage 51 by conduit 57, which then delivers the gas sample to the second stage 52. The end 58 of conduit 57 is located beneath scrubbing liquid 54 in the second stage 52.

Container 60 (FIG. 1) holds fresh scrubbing liquid 54. The scrubbing liquid is removed from container 60 by conduit 61 by means of pump 62 which delivers the scrubbing liquid through conduit 63 into the second stage 52. The scrubbing liquid overflows from the second stage 52 into conduit 64 which delivers the scrubbing liquid to the first stage 51. The scrubbing liquid overflows from the first stage 51 into conduit 65 which delivers the used scrubbing liquid to conduit 66 which then feeds the used scrubbing liquid to waste.

When the stack gas being sampled is to be analyzed for reduced sulfur gases, the scrubbing liquid selected desirably is one which will remove sulfur dioxide from the gas. A suitable scrubbing liquid for removing sulfur dioxide is an aqueous solution of citric acid and potassium citrate, buffered to a pH of about 5.4 to 5.6. Furthermore, when the gas sample fed through the scrubber flows at a rate of about 250 ml per minute, the scrubbing liquid is desirably fed countercurrent to the gas flow at a rate of about 1 to 2 ml per minute. Each stage 51 and 52 of the scrubber 55 will desirably hold about 150 ml. of scrubbing liquid.

By using a continuous scrubber, the scrubbing liquid is constantly replenished with new liquid. As a result, performance does not diminish with time as in a batch scrubber. Also, only a small amount of scrubbing liquid need be present to contact the gas sample since the activity of the liquid, being new, is always high. Furthermore, the ability to scrub with a small amount of liquid permits use of smaller equipment which, in turn, reduces the sample retention time in the scrubber.

Retention time not only depends upon the void areas in the apparatus but also on the equilibrium of the gas sample with the scrubbing liquid, which is a function of the vapor pressure of sample gas absorbed in the scrubbing liquid. Because some of the sample gas is always absorbed in the scrubbing liquid and since it takes time for equilibrium to be established, the response time of the apparatus to obtain an accurate analysis reading is affected. Only after equilibrium is established is an accurate reading obtained. By using the smaller equipment and less scrubbing liquid according to the invention, a much faster response time to a change in gas sample composition is obtained than with prior art equipment.

If a batch scrubber were to be used, test data shows at least 500 to 1000 ml of scrubbing liquid would be needed and that it would probably not last more than 36 hours. As scrubbing progresses in a batch scrubber the liquid performance decreases in efficiency so that it must be renewed. Also, the scrubber volume must be about twice the volume of scrubbing liquid to have proper head space. The large volume of liquid in the scrubber and the large scrubber space result in equilibrium being achieved only after the passage of considerable time, thus inherently causing a slow response time.

The scrubbed gas sample leaves the second stage 52 through conduit 71 which delivers the gas to a demistor vessel 72. Scrubbing liquid is separated from the gas sample in the demistor 72. The separated scrubbing liquid flows from the demistor 72 into conduit 73 which delivers it to conduit 66, and from there it is fed to a waste disposal means. The gas sample is removed from demistor 72 through conduit 74 by means of pump 75, which then feeds the gas sample to conduit 76. The gas sample flows through conduit 76 to an analyzer and flow meter 77 where the total reduced sulfur content of the gas sample is determined. An ITT Barton coulometric titration cell can be used as the analyzer. The gas sample is then fed through a flow meter so that the volume of the gas can be determined to calculate the amount of total reduced sulfur in the gases being vented through the stack. The pump 75 provides a vacuum so that the sample flows through conduit 50, both stages of the scrubber 55, as well as the demistor 72.

As shown in FIG. 3, the probe 10 is composed of several parts. Stainless steel pipe 80, which can be made any appropriate length, but usually will be about 3 feet long, is removably connected by threaded pipe plug 87 to coupling 79 in flange or plate 16. Bolts 78 removably mount flange or plate 16 on the end of junction box 13. The stainless steel tube 80 has an internal diameter of ½ inch. Mounted on the outer end of pipe 80 is a cylindrical porous plate filter 81 about 6 to 8 inches long. A coupling 85 threadably joins pipe 80 and filter 81 together. Plug 87 is put in the end of filter 81.

A right angle deflector shield 82 is mounted beneath the porous plate filter 81. Clips 83 are mounted by welding across the bisecting legs of the deflector shield 82. Hose clamps 84 hold one leg of each clip 83 tightly against each end of the porous plate 81. The deflector shield 82 prevents particles in the flue gas from directly impinging upon the porous plate filter 81.

Inside of the stainless steel pipe 80 is located stainless steel tube 86 which terminates in a socket drilled in pipe plug 87 to which it is secured by welding. The other end of tube 86, which can be ⅜ inch outside diameter, extends to a distance short of the plug 87 in the front end of the probe. Thus, the tube 86 has its end 89 about two or three inches from the end of the plug 87. Inside of tube 86 is located a ¼ inch outside diameter Teflon tube 90 which is readily removable. The ¼ inch outside diameter tube keeps the sample gas from contacting metal fittings associated with the probe and junction box 13. The inner Teflon tube 90 has its front end 91 extending slightly beyond the end 89 of tube 86. The tube 90 extends through a hole drilled in plug 87 into junction box 13 (FIG. 5) where it terminates in fittings 95. The gas sample is withdrawn through the end 91 of tube 90. No gas is removed through end 89 of tube 86.

Heatable conduit 20 is joined at one end to junction box 13 by a flexible cord connection 96. The two wires 29 in conduit 20 are suitably joined together to complete the electrical circuit, so as to provide heat through resistance to electrical flow in the wires.

The heatable conduit 20 extends to the generally remote junction box 22 (FIG. 6) to which it is connected by flexible cord connection 99. The wires 29 are connected to the wires 100 which extend to a suitable electrical power source. The tube 26 having a ⅜ inch outside diameter extends just slightly beyond the end of conduit 20. The ¼ inch tube 28 inside of tube 26, however, continues to fitting 105 from which a ¼ inch Teflon tube 106 extends. The tube 106 is joined at the other end to fitting 107, from which the ¼ inch Teflon tube 31 extends to the condenser 33 previously described.

Those parts of the described apparatus which come in contact with the gas sample are made of materials which are essentially nonreactive with the gas sample. Stainless steel or polytetrafluoroethylene are used to make many of the parts.

The apparatus and method provided by the invention are highly useful in process control. The apparatus can be operated continuously, rather than intermittently, twenty-four hours a day, and day after day, and the data obtained used in making factory process adjustments as required to have the flue gas meet environmental regulations.

Calibration of the apparatus provided by the invention should be done routinely to obtain accurate analytical results. Those skilled in the art of gas analysis using apparatus related to that described in this application will know how to conduct the desired calibration. However, a brief outline of suggested calibration operations is provided to aid use of the invention.

A first calibration check which can be conducted is a total system calibration. To conduct such a test a calibration gas can be introduced into conduit 28 at a rate greater than the sampling rate to insure complete purging of the probe. All other elements of the apparatus operate in their normal mode during this test. The length of this test can vary from a few minutes to an hour or so with the length of time being that needed to attain a satisfactory response.

A second calibration check is an analyzer or detector zero check. In this check, conduit 74 is blocked by a valve not shown and pure air is fed to conduit 74 so that it is pumped to the analyzer and flow meter. This test will insure that a falsely high reading is not being reported by the analyzer. Simultaneously with this test clean air can be introduced into conduit 35, above the branch to conduit 50, and forced back through the condenser, conduit 20 and out of probe 10 to remove any particulate build-up. A valve, not shown, would need to be placed in conduit 35, above conduit 50, and temporarily closed to effect this blow-back operation.

A third check is that of cell detection calibration. In this step a calibration gas mixture is fed by conduit 76 directly into the analyzer and flow meter 77. The test is continued until the analyzer response is satisfactory.

The foregoing detailed description has been given for clearness of understanding only, and no unnecessary limitations should be understood therefrom, as modifications will be obvious to those skilled in the art.

What is claimed is:

1. Apparatus for withdrawing a gas from a source and conditioning the gas for subsequent analysis for total reduced sulfur content, which comprises:
   a gas probe having an inlet for a stream of gas and an outlet therefor,
   a conduit, having electrical resistance means to provide heat to a gas stream flowing therein, extending from the probe outlet to a condenser,
   said condenser having a passage through which a gas stream can flow and be cooled by indirect heat exchange with a cooling fluid and vapor in the gas condensed to liquid,
   a second conduit from the condensor passage to a means for producing a vacuum which causes a gas stream to enter the probe and flow through the heatable conduit to and through the condenser passage and the second conduit,
   a third conduit for delivering a stream of gas from the second conduit to a scrubber to wash the gas stream with a scrubbing liquid,
   means for removing the gas stream from the scrubber and separating entrained scrubbing liquid, and
   means for pumping the scrubbed gas stream, from which scrubbing liquid has been removed, to an analyzer and flow meter.

2. Apparatus according to claim 1 in which a removable tube of substantially inert material is inside of the conduit extending from the probe to about the condenser for the gas stream to flow therethrough to maintain the gas stream out of other contact with the conduit.

3. Apparatus according to claim 1 in which the scrubber is a counter-current scrubber.

4. Apparatus according to claim 1 including a means to provide a cool fluid for use in the condenser to cool the gas stream by indirect heat exchange with a cooling fluid.

5. Apparatus according to claim 4 in which the means supplies cold air as the cooling fluid.

6. Apparatus according to claim 5 including a vortex cooler for supplying cold air to the condenser to cool the gas stream indirectly.

7. Apparatus according to claim 1 in which the means for producing a vacuum includes a means downstream thereof for venting a major portion of the gas stream to waste so that the third conduit conveys a remaining minor portion of the gas stream to the scrubber.

8. Apparatus according to claim 1 including a scrubbing liquid reservoir container and means to withdraw scrubbing liquid from the container and feed it continuously at a uniform rate once through the scrubber as the gas stream flows through the scrubber and then feed the used scrubbing liquid to waste.

9. Apparatus according to claim 8 in which the scrubber has at least two stages in series, conduit means communicates with the two stages for delivering scrubbing liquid from the downstream second stage to the upstream first stage, and the means to withdraw the scrubbing liquid from the container has means to feed it to the second stage.

10. Apparatus according to claim 9 including means to continuously drain scrubbing liquid from the first stage at about the same rate it is received therein from the second stage.

11. Apparatus according to claim 1 in which the means for producing a vacuum is an aspirator.

12. Apparatus according to claim 1 in which the third conduit communicates with the second conduit between the condenser and the means for producing a vacuum.

13. Apparatus according to claim 12 in which the second conduit is positioned to direct flow therethrough of condensed liquid from the condenser to a means downstream thereof for draining off the condensed liquid while avoiding flow of condensed liquid into the third conduit.

14. Apparatus according to claim 12 in which the third conduit is substantially smaller diametrically than the second conduit to thereby feed only a minor amount of the initial gas stream to the scrubber.

15. A method comprising:
withdrawing a stream of hot gas containing water vapor from a source believed to contain a gaseous reduced sulfur content,
continuously maintaining the withdrawn stream of hot gas at a temperature above the dew point temperature of the gas,
feeding the stream of hot gas to a condenser to condense the water vapor from the gas,
removing the condensed water with the stream of previously hot but now cooled gas from the condenser,
diverting a minor portion of the cooled gas stream, substantially devoid of water, to a scrubber,
scrubbing the cooled gas stream in the scrubber with a scrubbing liquid,
withdrawing the scrubbed gas stream from the scrubber,
separating residual scrubbing liquid from the scrubbed gas stream, and
feeding the scrubbed gas stream to an analyzer and flow meter to determine the total reduced sulfur content in the gas stream.

16. A method according to claim 15 in which the hot gas is cooled in the condensor by cold air from a vortex cooler.

17. A method according to claim 15 in which the water and a major portion of the cooled gas stream from the condenser are continuously fed to waste.

18. A method according to claim 15 in which the cooled gas stream is scrubbed by a once through continuous counter-current flow of scrubbing liquid and the used scrubbing liquid is fed to waste.

19. A method according to claim 18 in which the cooled gas stream is scrubbed in at least two stages with new scrubbing liquid fed first to the second stage and then from the second stage to the first stage located upstream.

20. A method according to claim 15 in which the scrubbing liquid is supplied to, and removed from, the scrubber at a uniform rate.

21. A method according to claim 15 in which the scrubbing liquid reacts with any sulfur dioxide in the gas stream to remove it therefrom.

* * * * *